(12) United States Patent
Rizk et al.

(10) Patent No.: US 10,799,255 B2
(45) Date of Patent: Oct. 13, 2020

(54) SHAPEABLE RE-ENTRY DEVICES AND ASSOCIATED SYSTEMS AND METHODS

(71) Applicant: ReFlow Medical, Inc., San Diego, CA (US)

(72) Inventors: Isa Rizk, San Diego, CA (US); John Fulkerson, Rancho Santa Margarita, CA (US); Mahmood Razavi, Orange, CA (US)

(73) Assignee: REFLOW MEDICAL, INC., San Diego, CA (US)

( * ) Notice: Subject to any disclaimer, the term of this patent is extended or adjusted under 35 U.S.C. 154(b) by 252 days.

(21) Appl. No.: 14/913,971

(22) PCT Filed: Aug. 27, 2014

(86) PCT No.: PCT/US2014/052991
§ 371 (c)(1),
(2) Date: Feb. 23, 2016

(87) PCT Pub. No.: WO2015/031525
PCT Pub. Date: Mar. 5, 2015

(65) Prior Publication Data
US 2016/0206334 A1 Jul. 21, 2016

Related U.S. Application Data

(60) Provisional application No. 61/870,554, filed on Aug. 27, 2013.

(51) Int. Cl.
*A61B 17/22* (2006.01)
*A61M 25/01* (2006.01)
(Continued)

(52) U.S. Cl.
CPC .......... *A61B 17/22* (2013.01); *A61B 17/3207* (2013.01); *A61M 25/0194* (2013.01);
(Continued)

(58) Field of Classification Search
CPC ...... A61M 25/0194; A61M 2025/0197; A61M 25/0041; A61M 25/0043; A61M 25/0067;
(Continued)

(56) References Cited

U.S. PATENT DOCUMENTS 6,165,188 A * 12/2000 Saadat ............... A61B 17/3207
604/22
8,202,246 B2  6/2012 Kugler et al.
(Continued)

FOREIGN PATENT DOCUMENTS

JP    2007503914    3/2005
JP    2011510795    8/2009
(Continued)

OTHER PUBLICATIONS

International Search Report and Written Opinion for International Application No. PCT/US2014/052991 filed Aug. 27, 2014, Applicant: ReFlow Medical, Inc., dated Dec. 5, 2014, 16 pages.
(Continued)

*Primary Examiner* — Wade Miles
*Assistant Examiner* — Kankindi Rwego
(74) *Attorney, Agent, or Firm* — Morgan, Lewis & Bockius LLP

(57) ABSTRACT

Methods for treating a patient using intravascular devices, systems, and methods are disclosed herein. One aspect of the present technology is directed to an intravascular device having an elongated member coupled to and extending between a handle and an angled distal portion. The distal portion is moveable between a first configuration having a first shape configured for intravascular delivery and a second configuration having a second shape, different than the first shape, that is configured for intravascular delivery.

19 Claims, 13 Drawing Sheets

(51) Int. Cl.
*A61B 17/3207* (2006.01)
*A61B 17/00* (2006.01)

(52) U.S. Cl.
CPC .............. *A61B 2017/003* (2013.01); *A61B 2017/00331* (2013.01); *A61B 2017/00946* (2013.01); *A61B 2017/22001* (2013.01); *A61B 2017/22071* (2013.01); *A61B 2017/22077* (2013.01); *A61B 2017/22095* (2013.01); *A61M 2025/0197* (2013.01)

(58) Field of Classification Search
CPC .......... A61M 25/0068; A61M 25/0069; A61M 25/0074; A61M 25/008; A61M 25/09; A61M 25/09041; A61M 25/0905; A61M 2025/09058; A61M 2025/09116; A61M 2025/09125; A61B 2017/22094; A61B 2017/22095
See application file for complete search history.

(56) References Cited

U.S. PATENT DOCUMENTS

| | | | | |
|---|---|---|---|---|
| 8,932,276 | B1* | 1/2015 | Morriss | A61B 17/1657 604/528 |
| 2001/0000041 | A1 | 3/2001 | Selmon et al. | |
| 2005/0049574 | A1 | 3/2005 | Petrick et al. | |
| 2007/0250105 | A1* | 10/2007 | Ressemann | A61B 17/12022 606/196 |
| 2009/0018566 | A1 | 1/2009 | Escudero et al. | |
| 2010/0274270 | A1 | 10/2010 | Patel et al. | |
| 2012/0253186 | A1 | 10/2012 | Simpson et al. | |
| 2013/0006167 | A1 | 1/2013 | Alvarez et al. | |
| 2013/0006173 | A1 | 1/2013 | Alvarez et al. | |
| 2013/0041392 | A1 | 2/2013 | Edwards et al. | |

FOREIGN PATENT DOCUMENTS

| | | |
|---|---|---|
| JP | 3179894 | 11/2012 |
| WO | WO 2015031525 | 3/2015 |

OTHER PUBLICATIONS

Exam Report for co-pending Australian Application No. 2014312387, Applicant: Reflow Medical, Inc., dated Oct. 5, 2016, 4 pages.
Exam Report for co-pending Canadian Application No. 2922338, Applicant: Reflow Medical, Inc., dated Feb. 20, 2017, 3 pages.
Office Action for co-pending Japanese Application No. 2016537824, Applicant: Reflow Medical, Inc., dated Mar. 22, 2017, 5 pages.
Supplementary European Search Report for co-pending European Patent Application No. 14839605.4, Applicant: Reflow Medical, Inc., dated Mar. 30, 2017, 10 pages.
Austrialian Examination Report 1 issued in co-pending Application No. AU 2014312387, Applicant: ReFlow Medical, Inc., dated Oct. 5, 2016, 4 pages.
International Search Report and Written Opinion for International Application PCT/US2014/052991, Applicant: ReFlow Medical, Inc., dated Dec. 5, 2014, 16 pages.
Office Action received for co-pending Chinese Application No. 201480056502.4, including English translation, Applicant: ReFlow Medical, Inc., dated Jul. 3, 2017, 23 pages.
Office Action received for co-pending Japanese Application No. 2016-537824, including English translation, Applicant: ReFlow Medical, Inc., dated Mar. 5, 2018, 13 pages.
Office Action received for co-pending Chinese Application No. 201480056502.4, including English translation, Applicant: ReFlow Medical, Inc., dated May 22, 2018, 15 pages.
European Office Action for Application No. 14839605.4, dated Sep. 30, 2019, 5 pages.

* cited by examiner

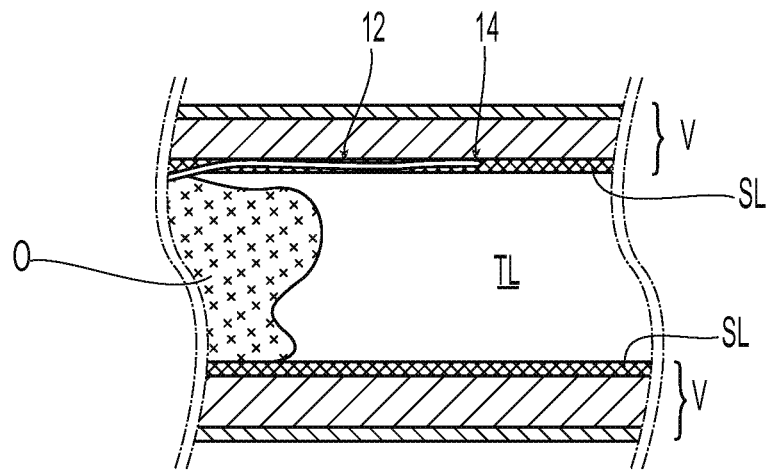
*Fig. 1D (Priort Art)*
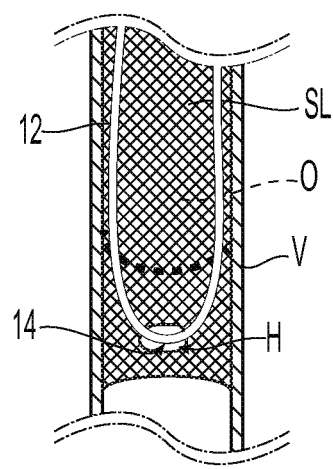
*Fig. 1E (Prior Art)*

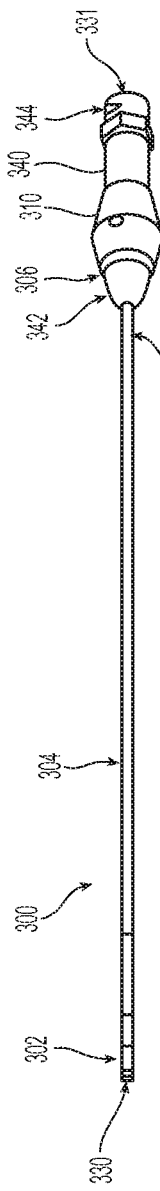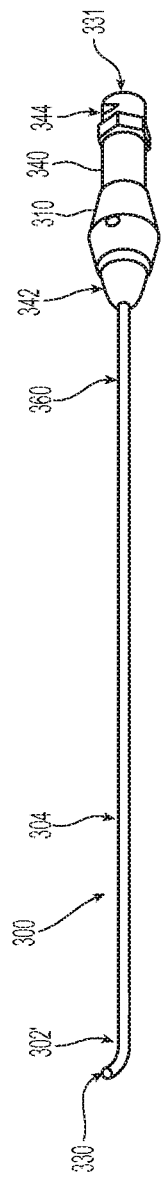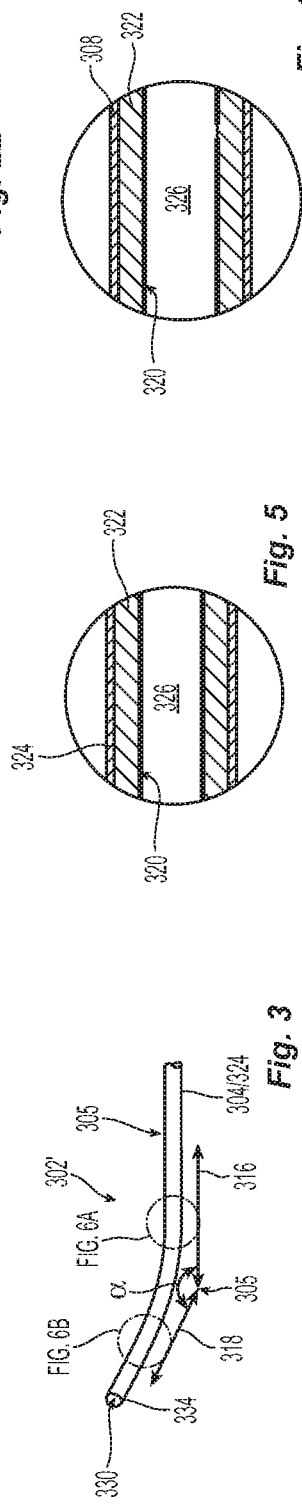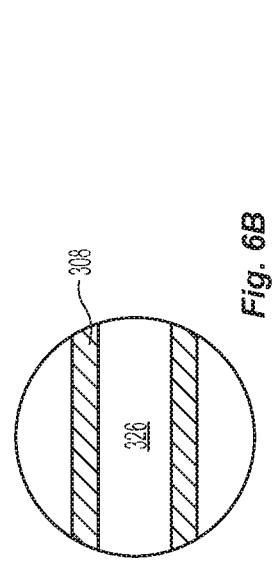

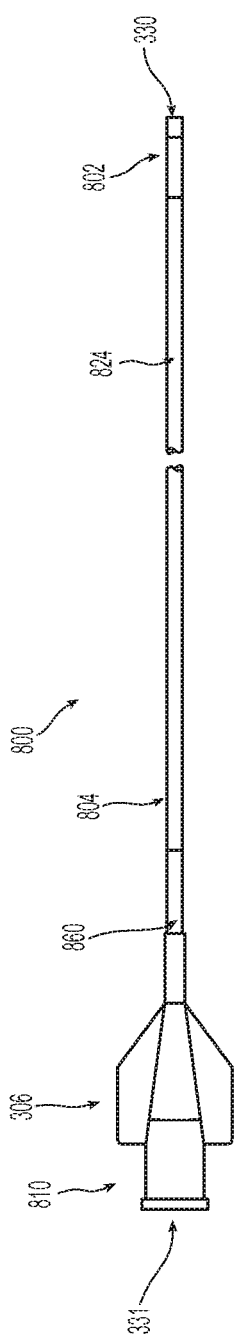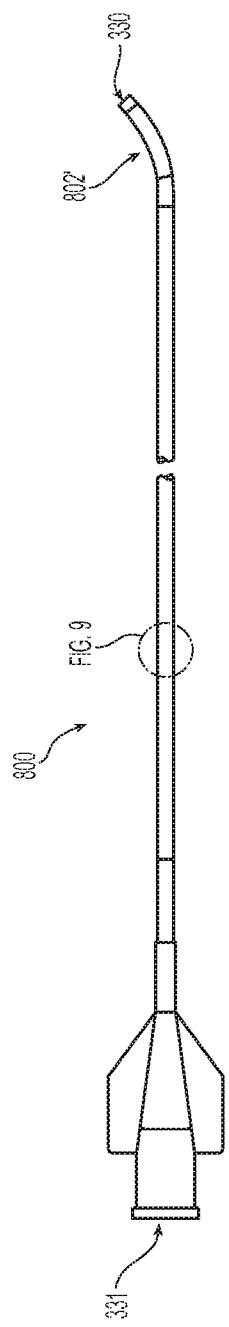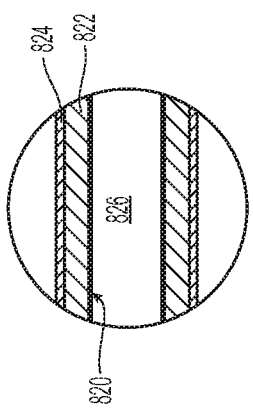

SHAPEABLE RE-ENTRY DEVICES AND ASSOCIATED SYSTEMS AND METHODS

TECHNICAL FIELD

This application is a National Stage of and claims the benefit of, International Application No PCT/US2014/052991, entitled "SHAPEABLE RE-ENTRY DEVICES AND ASSOCIATED SYSTEMS AND METHODS," filed Aug. 27, 2014, and which claims the benefit of U.S. Provisional Patent Application No. 61/870,554 filed Aug. 27, 2013, both of which are incorporated herein by reference in their entireties.

TECHNICAL FIELD

The present technology relates generally to systems, methods, and devices for accessing and/or treating vascular abnormalities and/or complications. In particular, several embodiments are directed to intravascular devices having shapeable distal portions for addressing occlusions within a body vessel, including those related to peripheral vascular disease states, cardiovascular diseases, cerebrovascular diseases, and others.

BACKGROUND

Chronic total occlusions ("CTO") are vascular lesions characterized by heavy atherosclerotic plaque within the blood vessel, resulting in complete (or nearly complete) obstruction of blood flow across the lesion. Such occlusions can occur anywhere in a patient's vascular system. Since most lesions form gradually over a long period of time, the ischemic tissue downstream of the lesion has time to form collateral circulation. For example, in the case of coronary arteries, collateral vessels can form from the proximal artery and connect into the distal artery ("ipsilateral collaterals"), or collateral vessels can form from the other major arterial branches and connect into the distal artery ("contralateral collaterals"). When the lesion finally becomes a total occlusion, the collateral circulation is typically sufficient to keep the distal tissue alive, though ischemic. Accordingly, it is desirable to reestablish blood flow through or around the blockage in blood vessels by crossing the CTO and advancing therapeutic devices, such as a balloon angioplasty catheter, to dilate and treat the CTO. Likewise, in some cases it may be necessary to cross a CTO to gain access to a location along the vasculature distal to the CTO.

CTOs are more difficult to cross than partially occluded lesions because, rather than navigate a pre-existing lumen, a guidewire must either penetrate the lesion or, when penetrating the occlusion is impractically difficult and/or complicated, go around the lesion via a sub-intimal layer of a vessel wall. FIGS. 1A-1F, for example, are schematic cross-sectional side views of a conventional device used to treat such a CTO. Referring first to FIG. 1A, a guidewire 12 and/or a catheter 10 is forced into a sub-intimal layer SL adjacent to an occlusion O. Once the guidewire 12 and/or catheter 10 traverse the occlusion O, the device(s) will require re-entry into a true lumen TL of the vessel V. For example, to re-enter the true lumen TL, many current techniques employ advancing the guidewire 12 such that it bends and/or loops back onto itself at its distal end 16 as the guidewire 12 is advanced distally through the sub-intimal layer SL. As best seen in FIGS. 1B and 1C, for example, such techniques can create a "sub-intimal tunnel" As best seen in FIGS. 1D-1F, once a looped end 14 of the guidewire 12 is distal to a distal end of the CTO, the guidewire 12 can be forced to re-enter the true lumen TL, thereby creating a large hole H and/or flap in the vessel wall V. Forcing re-entry utilizing a looped guidewire, however, may cause complications for the patient, such as unnecessarily extending the sub-intimal tunnel, perforation of the vessel V, and/or undesirable dissection of the vessel V that requires additional treatment.

Other current methods of re-entering the true lumen TL during treatment involve utilizing one of the currently available re-entry devices. Such re-entry devices, however, typically have larger diameters than the original tools utilized in the procedure. In many procedures, for example, the catheter in use is removed and the introducer sheath is replaced with a larger sheath (e.g., 7-8 Fr sheath). Such a transition, however, can cause significant disruptions to the procedure and dramatically increase procedure time and x-ray exposure for the patient.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure. Furthermore, components can be shown as transparent in certain views for clarity of illustration only and not to indicate that the illustrated component is necessarily transparent.

FIGS. 1A-1F are schematic cross-sectional side views of a conventional device used to treat a CTO by traversing the CTO via a sub-intimal space.

FIG. 2A is a side perspective view of an intravascular device in a low-profile configuration configured in accordance with an embodiment of the present technology.

FIG. 2B is a side perspective view of the intravascular device of FIG. 2A with an angled distal portion configured in accordance with an embodiment of the present technology.

FIG. 3 is an enlarged side view of the distal portion of the device of FIG. 2B without a guidewire and/or intravascular catheter placed therethrough.

FIG. 4 is an enlarged side view of the distal portion of the device of FIG. 2B with an intravascular catheter and guidewire placed therethrough in accordance with an embodiment of the present technology.

FIG. 5 is an enlarged cross-sectional view of a portion of the elongated member of the device shown in FIG. 7A configured in accordance with an embodiment of the present technology.

FIG. 6A is an enlarged cross-sectional view of a portion of the elongated member of the device shown in FIG. 3 configured in accordance with an embodiment of the present technology.

FIG. 6B is an enlarged cross-sectional view of another portion of the elongated member of the device shown in FIG. 3 configured in accordance with an embodiment of the present technology.

FIG. 7A is an enlarged side view of the intravascular device of FIG. 2B configured in accordance with the present technology.

FIG. 7B is an enlarged cross-sectional side view of the intravascular device of FIG. 2B mapped to FIG. 7A in accordance with the present technology.

FIG. 7C is a side view of a shaping mandrel configured in accordance with the present technology.

FIG. 8A is a partially-schematic side view of an intravascular device in a low-profile configuration, configured in accordance with an embodiment of the present technology.

FIG. 8B is a partially-schematic side view of the intravascular device of FIG. 8A having an angled distal portion configured in accordance with an embodiment of the present technology.

FIG. 9 is an enlarged cross-sectional view of a portion of the elongated member of the device shown in FIG. 8B in accordance with an embodiment of the present technology.

DETAILED DESCRIPTION

Figure 1A:
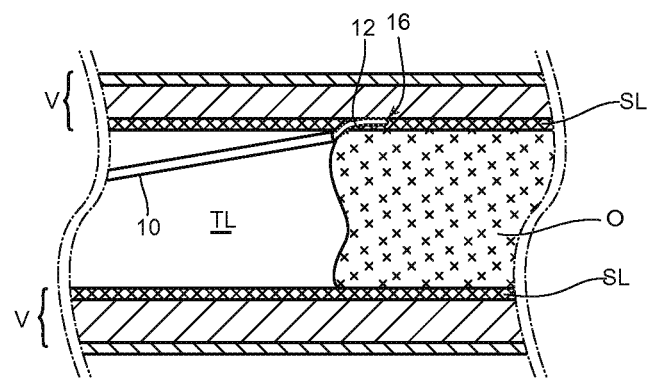
Figure 1B:
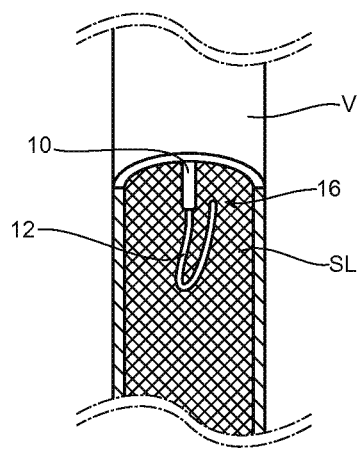
Figure 1C:
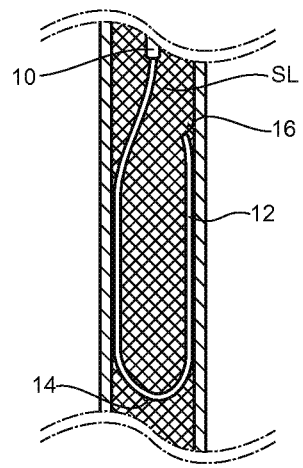
Figure 1F:
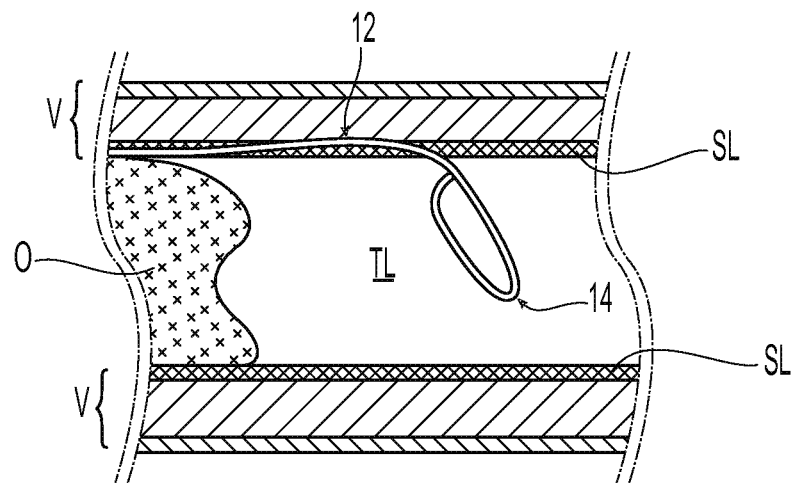

The present technology relates generally to systems, methods, and devices for crossing and treating CTOs. Specific details of several embodiments of the present technology are described herein with reference to FIGS. 2-17B. Although many of the embodiments are described below with respect to devices and methods for crossing and/or treating CTOs, any vascular occlusion in addition to those described herein may be crossed and/or treated within the scope of the present technology (e.g., full occlusions, partial occlusions, occlusions resulting from a thrombus, occlusions resulting from an embolism, occlusions resulting from atherosclerosis, etc.). Additionally, other embodiments of the present technology can have different configurations, components, or procedures than those described herein. For example, other embodiments can include additional elements and features beyond those described herein, or other embodiments may not include several of the elements and features shown and described herein.

For ease of reference, throughout this disclosure identical reference numbers are used to identify similar or analogous components or features, but the use of the same reference number does not imply that the parts should be construed to be identical. Indeed, in many examples described herein, the identically-numbered parts are distinct in structure and/or function.

Generally, unless the context indicates otherwise, the terms "distal" and "proximal" within this disclosure reference a position relative to an operator or an operator's control device. For example, "proximal" can refer to a position closer to an operator or an operator's control device, and "distal" can refer to a position that is more distant from an operator or an operator's control device.

I. Selected Embodiments

FIG. 2A is a side perspective view of an intravascular device 300 in a low-profile or generally straight configuration in accordance with an embodiment of the present technology. The intravascular device 300 can include proximal portion 306 having a handle 310, as well as a distal portion 302 and an elongated shaft 304 extending between the handle 310 and the distal portion 302. The handle 310 can be configured to be positioned at a location external to a patient, and the elongated shaft 304 can be configured to locate the distal portion 302 intravascularly at or near a complete or partial occlusion within a blood vessel of the patient. The intravascular device 300 can have a lumen 326 (FIG. 5) extending proximally from an opening 330 at a distal end of the device 300 to an outlet 331 at the handle 310 of the device 300.

FIG. 2B is a side view of the intravascular device 300 with the distal portion 302 in an angled or treatment configuration (labeled in FIG. 2B as 302'). In some embodiments, the distal portion 302 may be "cold-worked" during manufacturing into a permanent, angled shape. In other embodiments, the distal portion 302 of the intravascular device 300 in FIG. 2A may be composed of a malleable or shapeable material so that a clinician can manually transform the generally straight distal portion 302 into an angled distal portion 302'. For example, the intravascular device 300 can come as part of a kit that includes one or more shaping mandrels (see, for example, the mandrel 370 shown in FIG. 7C). The mandrels can come in a variety of configurations (e.g., different diameters, shapes, angles, etc.) to address different needs presented by the particular patient's vasculature. The clinician can place the mandrel at least partially within or over the distal portion 302 and bend or manipulate the distal portion 302 into the angle or shape of the mandrel. In some embodiments, the clinician can manually bend the distal portion 302 to a desired angle based on specific requirements presented by a particular procedure (e.g., crossing, steering, targeting for a particular area within the vasculature, etc.). For example, the clinician can manipulate the distal portion 302 without a mandrel, or in some embodiments, the mandrel can be flexible such that the mandrel bends with the distal portion 302 and primarily functions to keep the internal diameter of the distal portion 302 from collapsing or kinking during the shaping process.

Often times, the clinician may find it beneficial and/or necessary to utilize multiple shapes and/or angles during a procedure. As such, the distal portion 302 of the present technology is configured to be repeatedly angled, shaped, and/or manipulated during a procedure. For example, a clinician may initially utilize a first angle (for example, a 45° angle) or shape but realize, after inserting the device 300, that a greater angle (e.g., 70°, 60°, 50°, etc.), lesser angle (e.g., 30°, 20°, 15°, 10°, etc.), or different shape may be needed to navigate the vasculature and/or re-enter the true lumen. The clinician can remove the device 300 from the patient and bend, angle, shape, and/or otherwise manipulate the device to a second angle or shape that is different from the first angle or shape. The clinician can then re-insert the device 300 with the second angle or shape. The clinician can remove and re-shape or manipulate the distal portion 302 as many times as desired during a single procedure (e.g., 2 times, 3 times, 4 times, etc.). In some embodiments, the distal portion 302 can be bent at multiple portions along its longitudinal axis.

Although the shape of the distal portion 302 can be affected by the clinician and/or mandrel, once a desired shape is set the distal portion 302 has sufficient rigidity to retain its desired shape when subjected to tortuous anatomy or when a guidewire and/or interventional device is placed therethrough. The shapeable distal portion 302 can be made from shape memory plastic, Nitinol, stainless steel, titanium, tungsten, tantalum, Elgiloy, and other suitable materials. In some embodiments, the shapeable distal portion can be between about 0.25 inches to about 1.50 inches in length along its longitudinal axis. In some embodiments, the shapeable distal portion can be a different color than the remainder of the elongated shaft for identification purposes. In other embodiments, however, the shapeable distal portion may have a different arrangement and/or include different features.

Figure 7A:
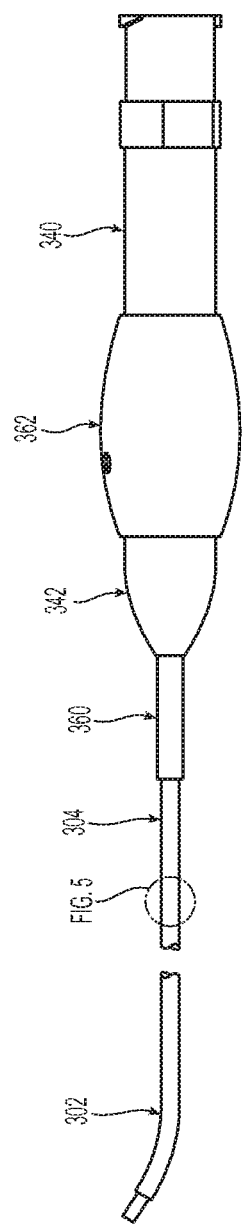
Figure 7B:
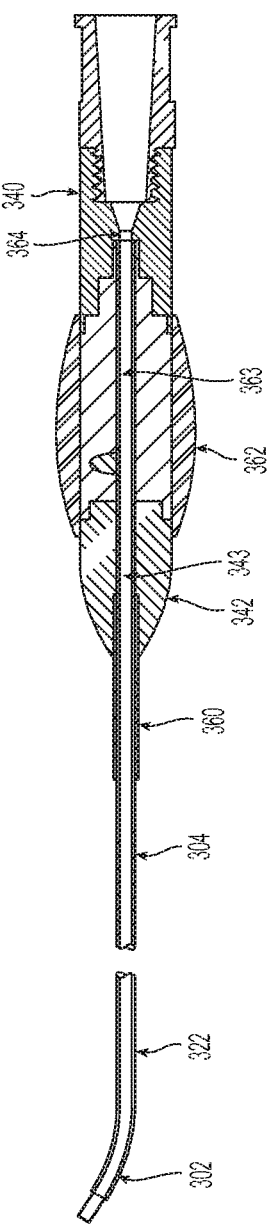
Figure 7C:
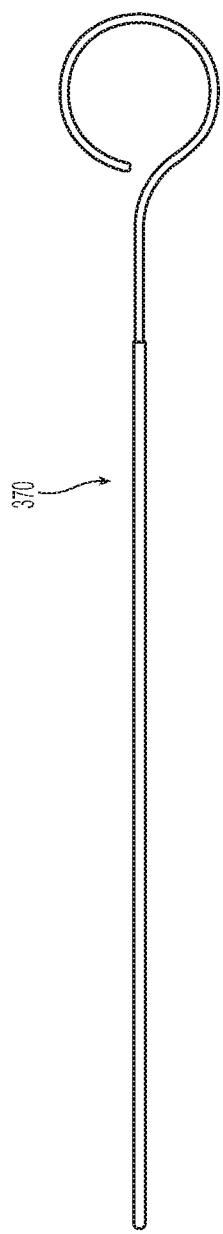

FIG. 5 is an enlarged cross-sectional view of a portion of the elongated shaft 304 proximal to the distal portion 302. FIGS. 7A and 7B show an enlarged side view and a partial cross-sectional side view, respectively, of the intravascular device of FIG. 2B. Referring to FIGS. 5, 7A and 7B together, the elongated shaft 304 may include one or more layers configured to rotate along a central axis independently of one another. For example, the elongated shaft 304 can include an outer sheath 324 and a tubular rotating member 322 within the outer sheath 324. As shown in FIG. 7B, a proximal section of the outer sheath 324 can be fixed to a first control knob 342 (e.g., at a first portion 343), and a proximal section of the rotating member 322 can be fixed to a second control knob 362 (e.g., at a second portion 363). Accordingly, rotational motion applied to the first knob 342 (e.g., by a clinician) causes rotation of the outer sheath 324, and rotation of the second knob 362 causes rotation of the rotating member 322. In some embodiments, a proximal region 360 of the outer sheath 324 is reinforced to provide strain relief to the outer sheath 324 and/or the rotating member 322 during rotation. The outer sheath 324 may be made of a flexible polymer (e.g., polyurethane, polyether block amide copolymer sold under the trademark PEBAX, etc.) or any suitable material, and may have an outer diameter of about 1.9 Fr to about 5 Fr. In other embodiments, however, the outer sheath 324 may have a different arrangement and/or include different features. The intravascular catheter can accommodate a range of guidewire sizes (e.g., 0.010 inches, 0.014 inches, 0.018 inches, 0.035 inches and 0.038 inches).

The rotating member 322 can be made of metal, plastic, and/or any suitable material with sufficient rigidity to adequately transfer rotational forces and/or provide accurate responsiveness at its distal end when actuated by a clinician located at a proximal portion 306 of the device 300. The rotating member 322 can be a solid, slotted, coiled, and/or braided tube (e.g., a braid-reinforced polyimide), and in some embodiments the rotating member 322 can have any suitable shape and/or configuration. In some embodiments, the intravascular device 300 may include a lubricious coating between the rotating member 322 and the outer sheath 324 to allow for friction free or relatively low friction manipulation of the rotating member 322 within the sheath 324 in various anatomical tortuosity. Without being bound by theory, it is believed that such layering renders the tortuosity impact on torsional response insignificant relative to torque transmission.

The inner lumen 326 of the rotating member 322 can be coated with a lubricous coating 320 (e.g., polytetrafluoroethylene (PTFE), fluorinated ethylene propylene (FEP), hydrophilic, etc.) applied directly to the inner walls of the rotating member 322. The inner lumen 326 extends distally from an opening 331 at the handle 310 to an opening 330 at a distal portion 302. The inner lining 320 allows for fluid, guidewires, and/or other intravascular devices (collectively referred to herein as "interventional devices D") to be slidably positioned within the lumen 326 of the rotating member 322. For example, the handle 310 can include an opening 331 for insertion of an interventional device such as the crossing device disclosed in International Patent Application No. PCT/US2010/047170, filed Aug. 30, 2010, entitled "SYSTEMS, METHODS AND DEVICES FOR ABLATION, CROSSING, AND CUTTING OF OCCLUSIONS," which is incorporated herein by reference in its entirety. In some embodiments, however, the handle 310 may have a different arrangement and/or include different features.

FIG. 3 is a side view of the distal portion 302 of the intravascular device 300 of FIG. 2B without an interventional device D placed therethrough, and FIG. 4 is a side view of the distal portion 302 including an interventional device D. Referring to FIGS. 3 and 4 together, the distal portion 302 can be a generally hollow tube having an attachment region 316 carried by, fixed to, and/or contiguous with a distal region 305 of the elongated shaft 304. The distal portion 302 can also include an angled region 318 extending distally at an angle $\alpha_0$ from the attachment region 316 and terminating at an atraumatic distal tip 334.

In some embodiments, the attachment region 316 of the distal portion 302 is attached to the rotating member 322 such that rotation of the rotating member 322 causes rotation of the distal portion 302. For example, as shown in FIG. 6A, the distal portion 302 can be defined by an angled tube 308, and at least a portion of the attachment region 316 of the angled tube can be placed over at least a portion of a distal region of the rotating member 322. The overlapping portions can then be joined together (e.g., via adhesive, crimping, soldering, etc.). The outer sheath 324 may be advanced over the rotating member 322 until a distal end of the outer sheath 324 comes in contact with a proximal end of the angled tube 308. Accordingly, the transition between the outer sheath 324 and the distal portion 320 may be seamless allowing for a low profile and maximum crossing ability.

In embodiments where the distal portion is not shapeable by the clinician, the distal portion 302 can be made from stainless steel, Nitinol, Elgiloy, other metals and/or similarly stiff materials that allow the distal portion 302 to retain its bent and/or angled shape while passing through the tortuous vasculature and/or when an interventional device (such as the interventional device D) is slidably positioned through the lumen 326 at or distal to a bend 350 in the distal portion 302. Many current devices have distal portions that are heat-treated to have an angled configuration. Such heat-treated devices, however, do not retain their shapes once an interventional device D is passed therethrough and/or the device is subject to a tortuous anatomy. In contrast with such current devices, the non-shapeable distal portion 302 of the present technology is not heat-treated, and rather comprises a hollow, stiff tube 308 that is "cold-worked" into a permanent, angled shape that is unaffected by anatomical tortuosity and/or placement of an interventional device D therethrough.

Regardless of whether the distal portion is shapeable or non-shapeable, the angle $\alpha_0$ remains the same even when an interventional device D is advanced through the lumen 326 of the distal portion 302 and extends through the opening 330 at the distal tip 334. Accordingly, the angled distal portion 302 allows for the predictable angulation of a separate intravascular device and/or guidewire, regardless of the shape of the separate intravascular device or the guidewire. Likewise, it is important to note that the angled distal portion 302 is not subject to any control wires and/or actuation device that can be manipulated at a proximal portion 306 of the device 300 to cause deflection at the distal portion 302. In some embodiments, all or a portion of the distal portion 302 may be coated with or comprised at least in part of radiopaque material to aid in positioning the device.

Even with the angled distal portion 302, the overall profile of the intravascular device 300 remains no greater than 7 Fr. In some embodiments, the overall profile of the intravascular device remains no great than 5 Fr. The angle $\alpha_0$ of the distal portion 302 can vary (e.g., between about 1 to about 90 degrees). In some embodiments, for example, the angle $\alpha_0$ is between about 10 and about 40 degrees. In other embodiments, the angle $\alpha_0$ is between about 25 degrees and about 35 degrees (e.g., about 25 degrees, about 30 degrees, about 35 degrees, etc.). In some embodiments, the distal portion 302 may be configured to have any suitable angle and/or length relative to the length of the intravascular device 300.

The distal tip 334 can be atraumatic and have a generally tapered shape. In some embodiments, the distal tip 334 can also be configured to engage another element of the intravascular device 300. For example, the opening 330 at the distal end of the distal tip 334 can define a passageway for receiving a guidewire (not shown) for delivery of the treatment device using over-the-wire ("OTW") or rapid exchange ("RX") techniques. In other embodiments, however, the distal tip 334 may have a different arrangement and/or include different features. The distal tip 334 may also be radiopaque to aid positioning of the device.

FIG. 8A is a side view of an intravascular device 800 in a low-profile or generally straight configuration configured in accordance with an embodiment of the present technology. The intravascular device 800 can include a handle or luer 810 at a proximal portion 306, a distal portion 802, and an elongated shaft 804 extending between the luer 810 and the distal portion 802. The luer 810 can be configured to be positioned at a location external to a patient, and the elongated shaft 804 can be configured to locate the distal portion 802 intravascularly at or near a complete or partial occlusion within a blood vessel of the patient. The intravascular device 800 can have a lumen 826 extending from an opening 330 at a distal end of the device 300 to an outlet 331 at the handle 310 of the device 300.

FIG. 8B is a side view of the intravascular device 800 with the distal portion 802 in an angled or treatment configuration 802'. In some embodiments, the distal portion 802 is "cold-worked" during manufacturing into a permanent, angled shape. In other embodiments, the distal portion 802 of the intravascular device 800 in FIG. 8A can be made of a malleable or shapeable material so that a clinician can manually transform the generally straight distal portion 802 into an angled distal portion 802'. For example, the intravascular device 800 can come as part of a kit that includes a shaping mandrel 370 (see FIG. 7C). The clinician may place the mandrel 370 at least partially within or over the distal portion 802 to keep the internal diameter of the distal portion 802 from collapsing or kinking while it is manually bent to the desired shape. In some embodiments, the clinician may manually bend the distal portion 802 to a desired angle based on specific requirements presented by a particular procedure (e.g., crossing, steering, targeting for a particular area within the vasculature, etc.). Although the shape of the distal portion 802 can be manipulated by the clinician, once a desired shape is set the distal portion 802' has sufficient rigidity to retain its desired shape when subjected to tortuous anatomy or with a guidewire and/or interventional device placed therethrough. The shapeable distal portion 802 can be made from shape member plastic, Nitinol, stainless steel, titanium, tungsten, Elgiloy, and others. The shapeable distal portion can be between about 0.25 inches to about 0.30 inches in length along its longitudinal axis.

FIG. 9 shows an enlarged cross-sectional view of the intravascular device of FIG. 8B. The elongated shaft 804 can include an outer layer 824 and a braid-reinforced polyimide layer 822 within the outer layer 824. During manufacturing, a polymer (e.g., polyether block amide copolymer sold under the trademark PEBAX) may be melted over the braid 822 to form the outer layer 824. In some embodiments, a proximal region 860 of the outer layer 824 can be reinforced by additional material (e.g., additional polyether block amide copolymer sold under the trademark PEBAX is melted onto the braid) to provide strain relief to the outer layer 824 when rotated. Rotational motion applied to the luer 810 (e.g., by a clinician) causes rotation of the outer layer 824 along the entire longitudinal axis of the elongated shaft 804. The outer sheath may be made of a flexible polymer (e.g., polyether block amide copolymer sold under the trademark PEBAX). The inner walls 826 of the braid may also include a lubricous coating 820 as described above.

The braided layer 822 may extend partially or completely along the longitudinal axis of the distal portion. The braided layer 822 is expected to provide a high burst strength (e.g., greater than or equal to 2000 psi) and additional kink resistance.

Figure 10:
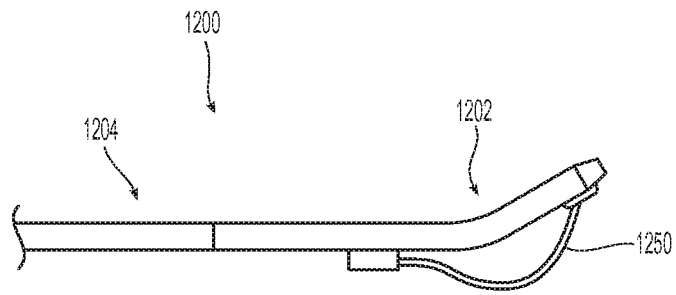
FIG. 10 is a side view of a distal portion of an intravascular device having a bracing member configured in accordance with another embodiment of the present technology.
Figure 11:
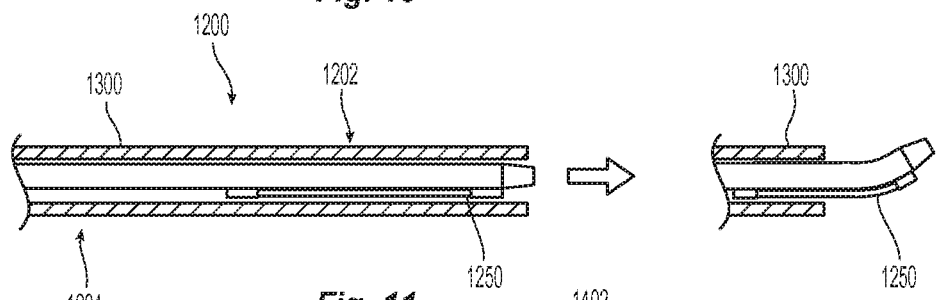
FIG. 11 is a partial cross-sectional side view of a distal portion of the intravascular device of FIG. 10 disposed within an outer sheath in accordance with the present technology.

FIG. 10 is a perspective view of a distal portion of an intravascular device 1200 having a bracing member 1250 configured in accordance with another embodiment of the present technology. In the illustrated embodiment, the bracing member 1250 can have a generally "humpback shape" configured to allow for additional deflection from the vessel wall. The bracing member 1250 can be made from metal and/or plastic materials. The bracing member 1250 can be delivered in a low-profile or delivery configuration, then expand upon proximal retraction of an outer sheath 1300 (see FIG. 11) to add additional support or stability to the distal portion 1202 of the intravascular device 1200. In some embodiments, the bracing member 1250 could automatically and/or manually extend and/or retract from a layer and/or lumen of the elongated shaft 1204 (e.g., the outer sheath 1224) to add stability. In some embodiments, the sheath 1300 can be partially retracted to selectively control the angle of the distal portion 1202 between about 0 and about 90 degrees.

Figure 12:
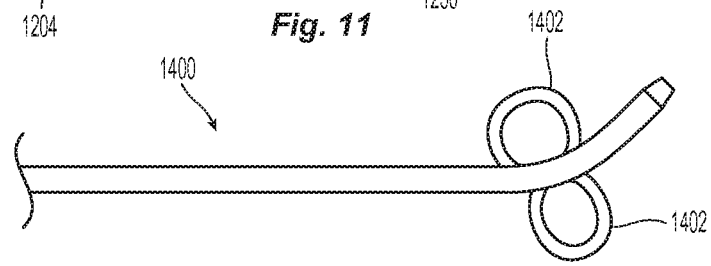
FIG. 12 is a side perspective view of a distal portion of an intravascular device having two inflatable support rings configured in accordance with the present technology.

FIG. 12 illustrates an intravascular device 1400 configured in accordance with another embodiment of the present technology. As shown in FIG. 12, the intravascular device 1400 may have one or more inflatable or expandable rings 1402 configured to position and support a distal portion 1404 of the device 1400 within the vessel. For example, once the distal portion 1404 is positioned at a target site, the rings 1402 can be expanded to force at least a portion of the distal portion 1404 away from an adjacent occlusion or vessel wall. In embodiments where the intravascular device includes a shapeable distal portion, expansion of the rings 1402 helps guide deflection of the distal portion. In embodiments where the intravascular device 1400 includes a pre-shaped distal portion, however, expansion of the rings 1402 does not generally affect angulation of the distal portion. Rather, in such embodiments, the rings 1402 may reinforce the pre-formed angle of the device 1400 and also stabilize the device with respect to the surrounding anatomy. In some embodiments, the rings 1402 can be independently expanded or deployed to provide additional directionality and/or stability to the device 1400.

Figure 13:
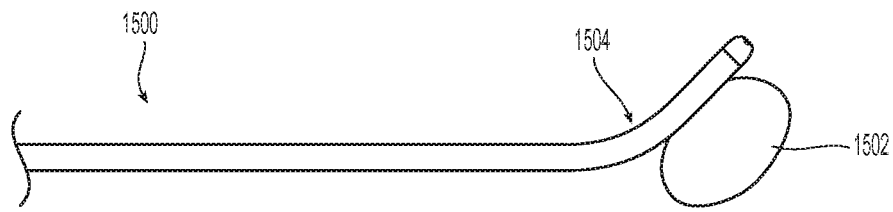
FIG. 13 is a side view of a distal portion of an intravascular device having a one-sided expandable member configured in accordance with the present technology.

FIG. 13 is a side view of another embodiment of an intravascular device 1500 having a one-sided expandable member 1502. Once expanded, the expandable member 1502 provides additional angulation to the distal portion 1504 and support to the device 1500. For example, in some embodiments, the expandable member 1502 aids in deflection of the distal portion 1504 off of the vessel wall and/or in redirecting the device 1500.

Figure 14:
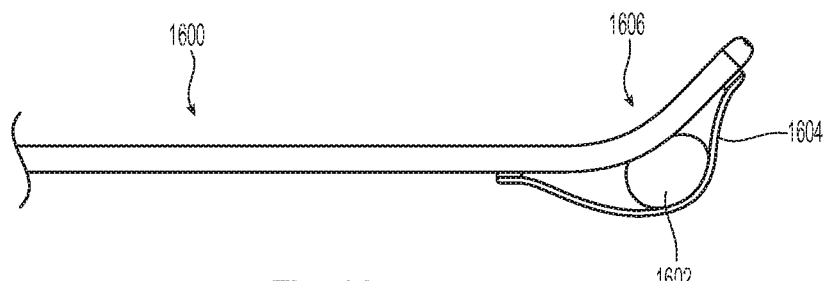
FIG. 14 is a side view of a distal portion of an intravascular device having a bracing member and an expandable member configured in accord ance with the present technology.

FIG. 14 shows yet another embodiment of an intravascular device 1600 having a combination of expandable members 1602 (e.g., balloons, inflatable rings, etc.) and a brace 1604. Such a combination is expected to provide both directionality and stability to the distal portion 1606. The expandable members 1602 may be inflated or expanded independent from deployment of the brace 1604. In some embodiments, an expandable member 1602 may be inflated or deflated, thereby allowing the pre-formed wire 1604 to bend and provide an additional angle to the device 1600. In some embodiments, the rings 1602 and/or pre-formed wire 1604 can also be sheathed for delivery through the vasculature until the distal portion of the device is positioned at a desired location inside the vessel, as discussed above with reference to FIGS. 12 and 13.

II. Selected Delivery Systems and Methods

The ability to percutaneously access the remote vasculature is well-known and described in the patent and medical literature. Once percutaneous access is achieved (for example, through the femoral or iliac veins), the interventional tools and supporting catheter(s) may be advanced to the target vessel or CTO and positioned at or proximate to the CTO in a variety of manners, as described herein.

Figure 17A:
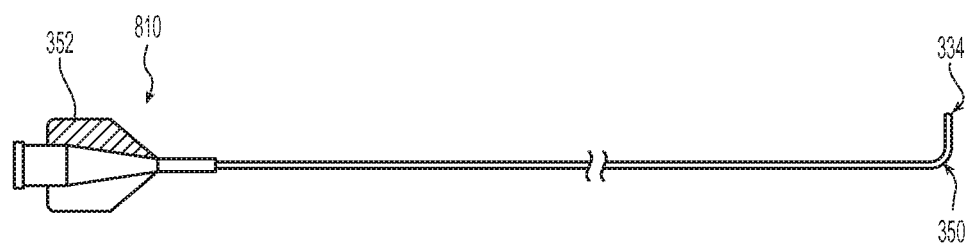
FIGS. 17A and 17B are side views of a proximal marker configured in accordance with another embodiment of the present technology.
Figure 17B:
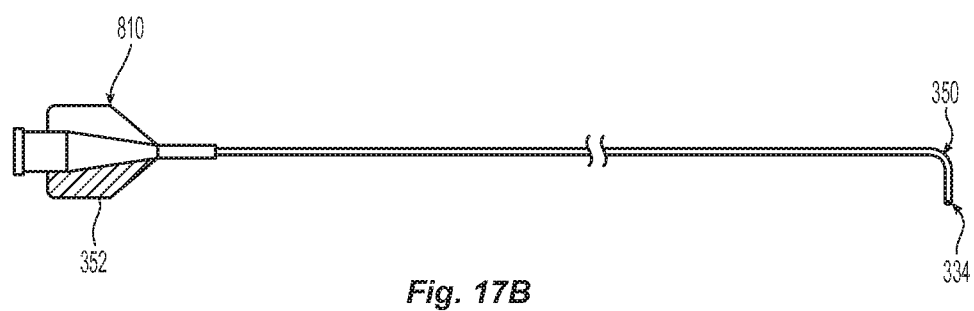

FIGS. 17A-17G illustrate one example for using an intravascular device 300 and/or one or more interventional devices to cross and/or treat a CTO. Referring first to FIG. 17A, a guidewire 800 may be advanced along the vasculature until the guidewire 800 is precluded from further distal movement by a proximal region of the CTO and inadvertently or purposely enters the sub-intimal layer SL (FIG. 17B). At this point, as best seen in FIG. 17C, the distal portion 302 of the device 300 can be advanced distally over the guidewire 800 and into the sub-intimal layer SL. As shown in the top view of FIG. 17D, once in the sub-intimal layer, the angled distal portion 302 can be advanced distally through the sub-intimal layer SL until the distal portion 302 of the device 300 is positioned at or distal to a distal end of the CTO. While the angled distal portion 302 is moved through the sub-intimal space, the angled region 318 is generally perpendicular to a true lumen TL of the vessel V.

The distal portion 302 can be advanced through the sub-intimal layer SL using known imaging systems and techniques such as fluoroscopy, x-ray, MRI, ultrasound or others. Radiopaque material can be incorporated into the guidewire 800, distal portion 302, and/or along any portion of the intravascular device 300 to provide additional visibility under imaging guidance. Such marker materials can be made from tungsten, tantalum, platinum, palladium, gold, iridium, or other suitable materials.

Once the distal portion 302 reaches the distal end of the CTO, the clinician can actuate the knob 362 (FIGS. 2A-2B and 7A-7B) or rotate the handle (FIGS. 8A and 8B) to rotate the distal portion 302 (via the rotating member 322) so that the angled region 318 is directed towards the true lumen TL of the vessel V, as shown in the top and side views of FIGS. 17E-17F, respectively.

As shown in FIGS. 16A and 16B and FIGS. 17A and 17B, in particular embodiments, the intravascular device may include a marking 352 on the luer or handle that aligns with the bend 350 such that a clinician can identify (from an extracorporeal location) the direction of the angle $\alpha_0$ and/or projection of the angled region 318. For example, the knob 362 may have a marking 352 at a circumferential position corresponding with the bend 350.

Figure 15A:
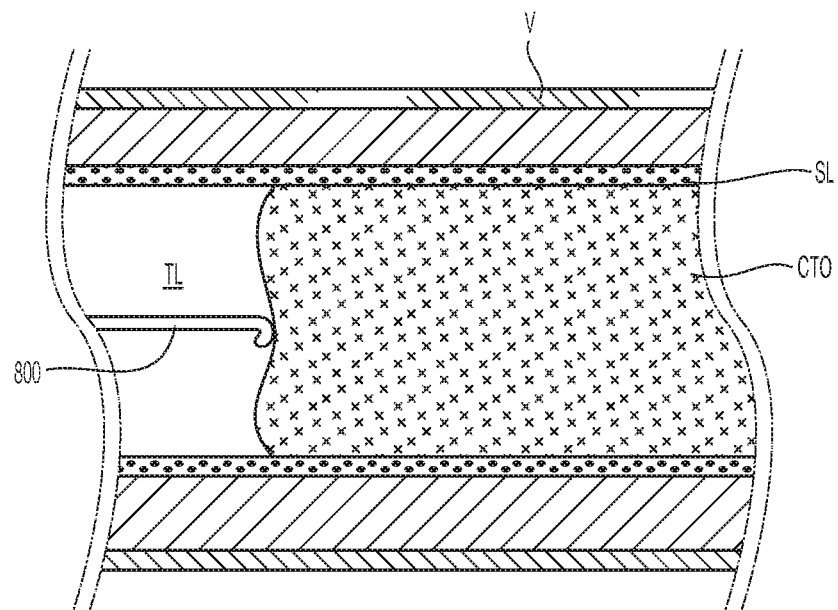
FIGS. 15A-15G are anatomical cross-sectional side views illustrating a method for using an intravascular device and/or one or more interventional devices for crossing and/or treating a CTO in accordance with an embodiment of the present technology.
Figure 15B:
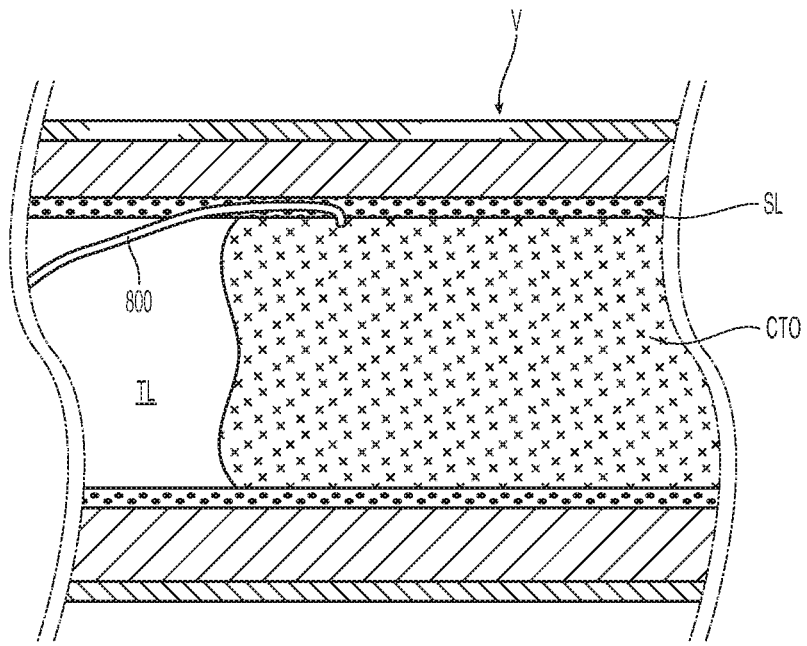
Figure 15C:
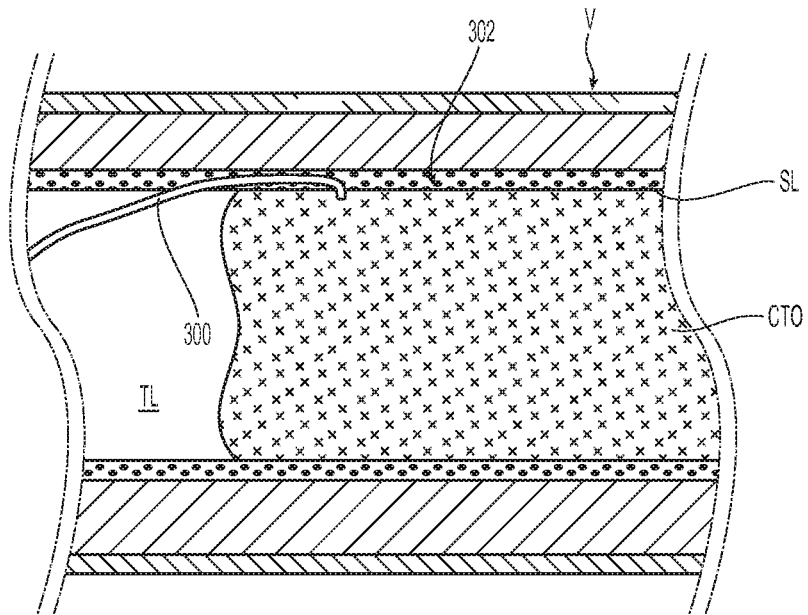
Figure 15D:
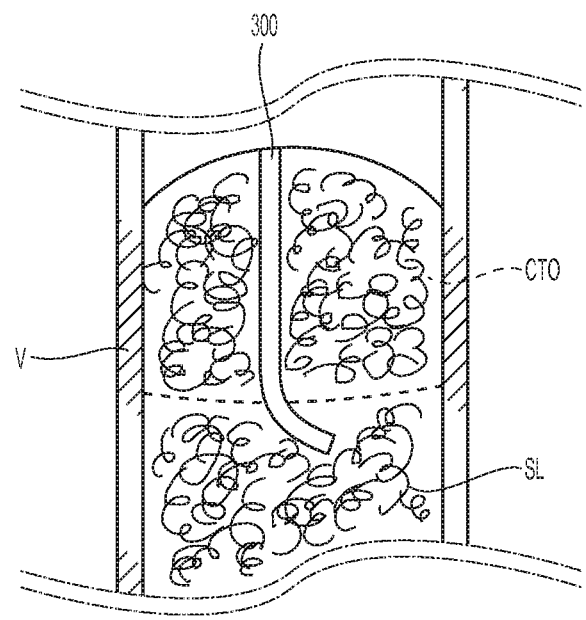
Figure 15E:
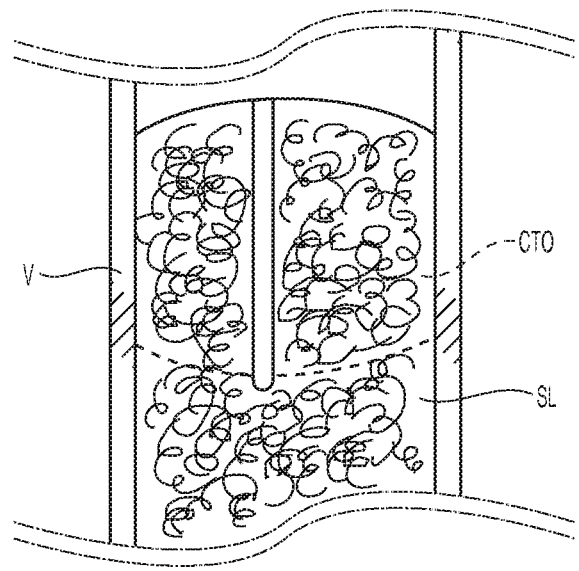
Figure 15F:
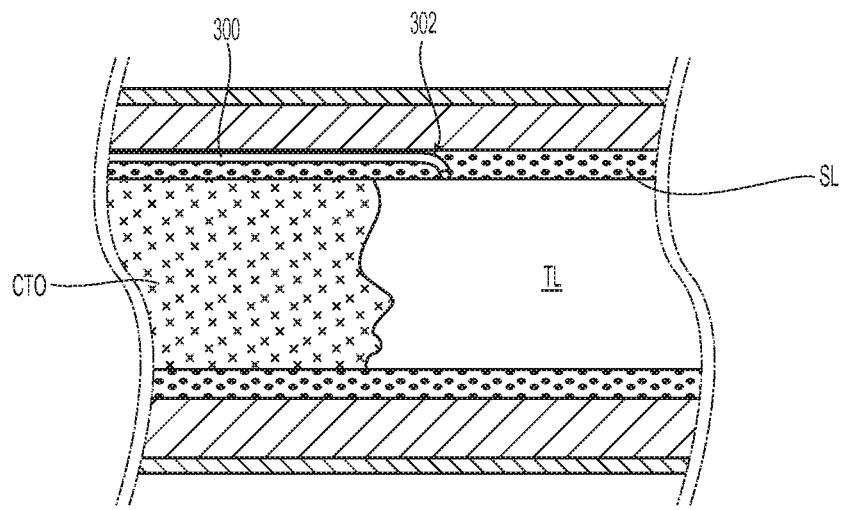
Figure 15G:
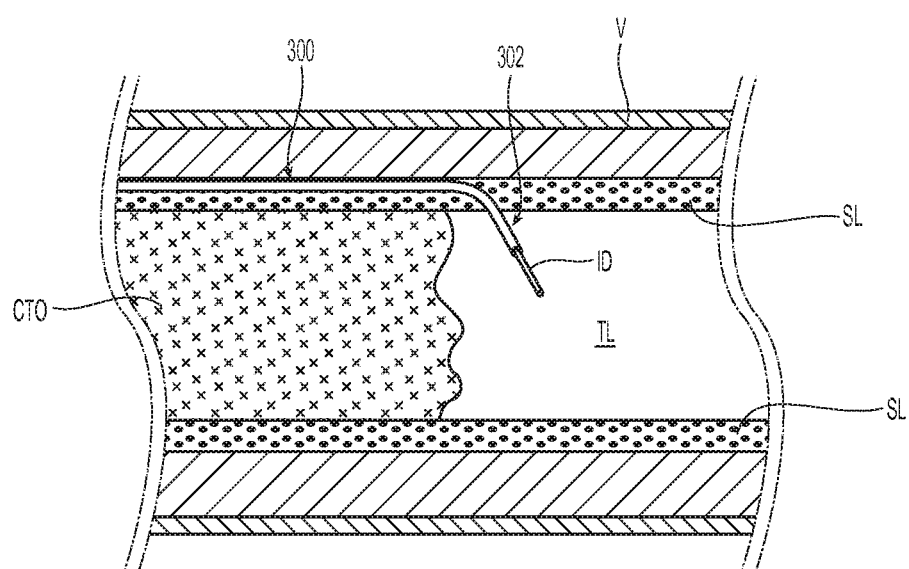
Figure 16A:
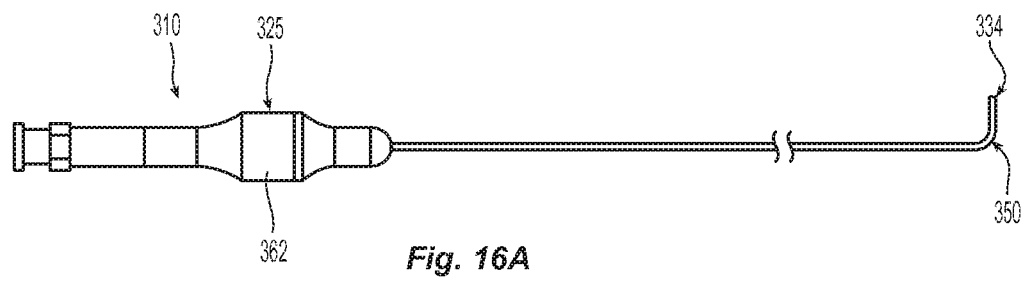
FIGS. 16A and 16B are side views of a proximal marker configured in accordance with embodiments of the present technology.
Figure 16B:
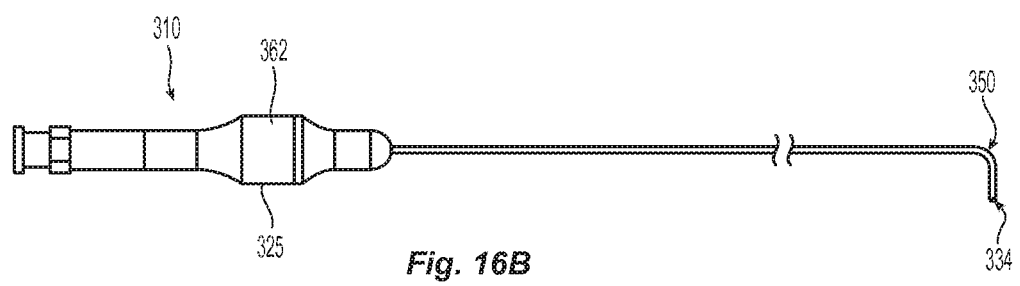

A piercing element (not shown) can be advanced through the distal portion 302 to penetrate the sub-intimal lining and facilitate re-entry into the true lumen TL. As discussed above, a guidewire 800 and/or an interventional device ID can be advanced through the opening 330 and into the true lumen TL of the vessel V in a direction and/or angle dictated by the angle $\alpha_0$ of the distal portion 302 (as best seen in FIG. 15G).

In some embodiments the intravascular device 300 can include one or more distal markers that could be utilized by the various imaging techniques described above. For example, in some embodiments, the distal portion 302 could have markings (e.g., holes, grooves, radiopaque markings, etc.) along its length so that when an interventional device reaches the distal portion 302, corresponding markings on the interventional device will align and confirm that the guidewire and/or interventional device have reached the distal portion 302 of the device 300. Additionally, such distal markings could be utilized when the device is used as a diagnostic catheter or angiographic catheter. Saline or dye could be flushed through the device and out the distal portion through the various holes.

It should be noted that the intravascular device described herein is not limited to a re-entry device. For example, various embodiments of the present technology could also be used when trying to reach areas of the vasculature with tortuosity and/or to provide steering while traversing such anatomy. Because the angled shape of the distal portion stays true and does not lose its configuration, multiple wires and other devices could be fed through the elongated shaft from an opening 331 at the proximal portion 306 and selectively positioned without the concern of having to compensate for any changes to the pre-set dimensions prior to entering the anatomy. In some embodiments, for example, the system may be used to reach a complex location having multiple bends, twists, and anatomical variability.

III. Examples

The following examples are illustrative of several embodiments of the present technology:

1. An intravascular device, comprising:
   a handle at a proximal portion;
   an elongated member coupled to and extending between the handle and an angled distal portion, wherein the elongated member includes—
   an outer sheath; and
   a hollow rotational member with the sheath, wherein the rotational member is coupled to the angled distal portion, and wherein rotation of the rotational member directly causes rotation of the angled distal portion; and
   wherein the angled distal portion—
   defines a lumen therethrough,
   has a first section and a second section that extends distally at an angle from the first section, and
   the angle between the first section and the second section remains the same when an interventional device is at least partially within the lumen of the distal portion and spans at least a portion of the first section and at least a portion of the second section.
2. An intravascular device, comprising:
   a handle at a proximal portion;
   an elongated member coupled to and extending between the handle and a distal portion, wherein the elongated member includes—
   an outer sheath; and
   a hollow rotational member with the sheath, wherein the rotational member is coupled to the distal portion, and wherein rotation of the rotational member directly causes rotation of the distal portion; and
   wherein, in response to a force applied by a clinician while the distal portion is located external to the patient, the distal portion is moveable between:
   a first configuration that is configured to be intravascularly delivered; and
   a second configuration that is configured to be intravascularly delivered, and wherein the second configuration is different from the first configuration.
3. The device of example 1 wherein the angle between the first section and the second section remains the same when a guidewire is at least partially within the lumen of the distal portion.
4. The device of any of examples 1-3 wherein the distal portion is not heat set.
5. The device of any of example 1 wherein the angle is about 30 degrees.
6. The device of any of examples 1-5 wherein the distal portion further comprises an atraumatic distal tip.
7. The device of any of examples 1-6 wherein—
   the rotational member has a distal end and a proximal end;
   the distal end of the rotational shaft is coupled to the distal portion; and
   the proximal end of the rotational shaft is coupled to a knob located at the handle.
8. The device of any of examples 1-7 wherein at least a portion of the distal portion is radiopaque.
9. The device of any one of examples 2, 4 and 6-8 wherein—
   the first configuration makes a first angle with respect to the longitudinal axis of the elongated member; and
   the second configuration makes a second angle with respect to the longitudinal axis of the elongated member, wherein the second angle is different than the first angle.
10. The device of any one of examples 2, 4 and 6-8 wherein—the first configuration is a rounded configuration having a first diameter; and the second configuration is a rounded configuration having a second diameter that is different than the first diameter.
11. The device of any one of examples 2, 4 and 6-8 wherein—
    the first configuration is a rounded configuration;
    the second configuration is a bent configuration.
12. The device of any one of examples 2, 4 and 6-11 wherein the distal portion is further moveable to a third configuration that is different than at least one of the first configuration and the second configuration.
13. The device of any one of examples 2, 4 and 6-11 wherein—
    the distal portion is further moveable to a third configuration that is different than the first configuration and the second configuration, and
    when in the third configuration, the distal portion is configured to be intravascularly delivered.
14. A method of using a treatment device having a distal portion, the method comprising:
    intravascularly delivering a distal portion in a first configuration;
    removing the distal portion in the first configuration to an extracorporeal location;
    reconfiguring the distal portion into a second configuration that is different than the first configuration; and
    intravascularly delivering the distal portion in a second configuration.
15. The method of example 14 wherein the first configuration is a rounded configuration having a first diameter and the second configuration is a rounded configuration having a second diameter that is different than the first diameter.
16. The method of example 14 wherein the first configuration makes a first angle with respect to the longitudinal axis of the treatment device and the second configuration makes a second angle with respect to the longitudinal axis of the treatment device, wherein the second angle is different than the first angle.
17. The method of example 14 wherein reconfiguring the distal portion includes bending the distal portion.
18. The method of any one of examples 14-17 wherein intravascularly delivering the device includes delivering the distal portion to an intravascular location proximate to a chronic total occlusion.
19. The method of any one of examples 14-18, further comprising:
    removing the distal portion in the second configuration to an extracorporeal location; reconfiguring the distal portion into a third configuration that is different than at least one of the first configuration and the second configuration; and intravascularly delivering the distal portion in a third configuration.

IV. Conclusion

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. An intravascular device comprising:
a handle;
an elongated shaft coupled to a distal end of the handle and comprising:
a first length of a braid-reinforced polymer layer; and
an outer layer over the first length of the braid-reinforced polymer layer, the outer layer comprising a polymer;
a distal portion coupled to a distal end of the elongated shaft and comprising:
a second length of the braid-reinforced polymer layer; and
a hollow tube over the second length of the braid-reinforced polymer layer, an entirety of the hollow tube being positioned distal to a terminal distal end of the outer layer, the hollow tube comprising a metal and being configured to be shaped to form a first section and a second section that extends distally at an angle from the first section such that the angle between the first section and the second section remains the same when an interventional device is at least partially within and spanning at least a portion of the first section and at least a portion of the second section; and
a distal tip coupled to a distal end of the distal portion and being tapered to form an atraumatic end, wherein the elongated shaft, the distal portion, and the distal tip define a lumen extending there through.

2. The intravascular device of claim 1 wherein the angle between the first section and the second section remains the same when a guidewire is at least partially within the lumen of the distal portion.

3. The intravascular device of claim 1 wherein the distal portion is not heat set.

4. The intravascular device of claim 1 wherein at least a portion of the distal portion is radiopaque.

5. The intravascular device of claim 1, wherein inner walls of the braid-reinforced polymer layer include a lubricous coating.

6. The intravascular device of claim 1, wherein the polymer of the outer layer is different than a polymer of the braid-reinforced polymer layer.

7. The intravascular device of claim 1, wherein the distal portion has a color that is different than a color of the elongated shaft.

8. The intravascular device of claim 1, wherein the braid-reinforced polymer layer and the distal portion are rotatable relative to the outer layer.

9. An intravascular device comprising:
a handle;
an elongated shaft coupled to a distal end of the handle and comprising:
a first length of a braid-reinforced polymer layer; and
an outer layer over the first length of the braid-reinforced polymer layer, the outer layer comprising a polymer;
a distal portion coupled to a distal end of the elongated shaft and comprising:
a second length of the braid-reinforced polymer layer; and
a hollow tube over the second length of the braid-reinforced polymer layer, a terminal proximal end of the hollow tube abutting a terminal distal end of the outer layer, the hollow tube comprising a metal and being configured to be shaped such that, in response to a force applied by a clinician while the distal portion is located external to a patient, the distal portion is moveable between:
a first configuration that is configured to be retained while the intravascular device is intravascularly delivered through tortuous anatomy; and
a second configuration that is configured to be retained while the intravascular device is intravascularly delivered through tortuous anatomy, and wherein the second configuration is different from the first configuration; and
a distal tip coupled to a distal end of the distal portion and being tapered to form an atraumatic end, wherein the elongated shaft, the distal portion, and the distal tip define a lumen extending there through.

10. The intravascular device of claim 9 wherein:
the first configuration makes a first angle with respect to a longitudinal axis of the elongated shaft; and
the second configuration makes a second angle with respect to the longitudinal axis of the elongated shaft, wherein the second angle is different than the first angle.

11. The intravascular device of claim 9 wherein:
the first configuration is a rounded configuration having a first diameter; and
the second configuration is a rounded configuration having a second diameter that is different than the first diameter.

12. The intravascular device of claim 9 wherein:
the first configuration is a rounded configuration; and
the second configuration is a bent configuration.

13. The intravascular device of claim 9 wherein the distal portion is further moveable to a third configuration that is different than at least one of the first configuration and the second configuration.

14. The intravascular device of claim 9 wherein the distal portion is further moveable to a third configuration that is different than the first configuration and the second configuration, and wherein, when in the third configuration, the distal portion is configured to be intravascularly delivered.

15. The intravascular device of claim 9, wherein at least a portion of the distal tip is radiopaque.

16. The intravascular device of claim 9, wherein inner walls of the braid-reinforced polymer layer include a lubricous coating.

17. The intravascular device of claim 9, wherein the polymer of the outer layer is different than a polymer of the braid-reinforced polymer layer.

18. The intravascular device of claim 9, wherein the distal portion has a color that is different than a color of the elongated shaft.

19. The intravascular device of claim 9, wherein the braid-reinforced polymer layer and the distal portion are rotatable relative to the outer layer.

* * * * *